United States Patent
Kang et al.

(10) Patent No.: US 10,648,988 B2
(45) Date of Patent: *May 12, 2020

(54) METHODS FOR PROVIDING INFORMATION RELEVANT TO DIAGNOSIS OF NEURODEGENERATIVE DISORDER

(71) Applicant: KOREA INSTITUTE OF SCIENCE AND TECHNOLOGY, Seoul (KR)

(72) Inventors: Ji Yoon Kang, Seoul (KR); Kyeong-Sik Shin, Seoul (KR); Jae-hoon Ji, Seoul (KR); Youhee Heo, Seoul (KR); Kyoseon Hwang, Seoul (KR); Myung-Sic Chae, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/878,351

(22) Filed: Jan. 23, 2018

(65) Prior Publication Data

US 2018/0238910 A1 Aug. 23, 2018

(30) Foreign Application Priority Data

Feb. 22, 2017 (KR) .................. 10-2017-0023470

(51) Int. Cl.
| | | |
|---|---|---|
| *G01N 33/53* | (2006.01) | |
| *G01N 25/18* | (2006.01) | |
| *G01N 24/00* | (2006.01) | |
| *G01N 27/00* | (2006.01) | |
| *G01N 33/68* | (2006.01) | |
| *A61B 5/145* | (2006.01) | |
| *A61B 5/1468* | (2006.01) | |
| *A61B 5/00* | (2006.01) | |
| *A61B 5/1486* | (2006.01) | |
| *C12Q 1/6883* | (2018.01) | |

(52) U.S. Cl.
CPC ....... *G01N 33/6896* (2013.01); *A61B 5/1468* (2013.01); *A61B 5/1486* (2013.01); *A61B 5/14507* (2013.01); *A61B 5/14546* (2013.01); *A61B 5/4088* (2013.01); *C12Q 1/6883* (2013.01); *C12Q 2600/158* (2013.01); *G01N 2333/4709* (2013.01); *G01N 2800/2821* (2013.01); *G01N 2800/52* (2013.01)

(58) Field of Classification Search
None
See application file for complete search history.

(56) References Cited

FOREIGN PATENT DOCUMENTS

| KR | 10-0595494 B1 | 7/2006 |
|---|---|---|
| KR | 10-2016-0034434 A | 3/2016 |

OTHER PUBLICATIONS

Massimo S. Fiandaca et al., "Identification of pre-clinical Alzheimer's disease by a profile of pathogenic proteins in neutrally-derived blood exosomes: a case-control study", Alzheimers Dement., Jun. 2015, pp. 600-607, vol. 11, No. 6.

Myung-Sic Chae et al., "Enhancing surface functionality of reduced graphene oxide biosensors by oxygen plasma treatment for Alzheimer's disease diagnosis", Biosensors and Bioelectronics, Oct. 21, 2016, pp. 1-8.

*Primary Examiner* — Olga N Chernyshev
(74) *Attorney, Agent, or Firm* — Rabin & Berdo, P.C.

(57) ABSTRACT

A method for providing information relevant to the diagnosis of a neurodegenerative disorder. The method includes (i) obtaining a biological sample containing vesicles from a subject, (ii) measuring the level of amyloid beta in the biological sample using an antibody specific for the N-terminus of amyloid beta, and (iii) comparing the measured level of amyloid beta in the biological sample with the level of amyloid beta in a previously prepared control sample.

8 Claims, 10 Drawing Sheets

METHODS FOR PROVIDING INFORMATION RELEVANT TO DIAGNOSIS OF NEURODEGENERATIVE DISORDER

CROSS-REFERENCE TO RELATED APPLICATIONS

This application claims priority under 35 U.S.C. § 119 to Korean Patent Application No. 10-2017-0023470 filed on Feb. 22, 2017 in the Korean Intellectual Property Office, the disclosure of which is incorporated herein by reference in its entirety.

BACKGROUND OF THE INVENTION

1. Field of the Invention

The present invention relates to methods for providing information relevant to the diagnosis of a neurodegenerative disorder, and more specifically to methods, kits, and devices for the diagnosis of Alzheimer' s disease. Particularly, the present invention relates to the diagnosis of Alzheimer's disease based on the analysis of amyloid beta extracted from neural exosomes.

2. Description of the Related Art

Alzheimer's disease is a neurodegenerative disorder known to cause brain dysfunction and even death. A proposed mechanism for Alzheimer's disease is as follows. When amyloid precursor protein is cleaved from the cell membrane, amyloid beta (amyloid-β or Aβ) responsible for Alzheimer's disease accumulates and activates mitochondrial division to generate reactive oxygen species (ROS). The reactive oxygen species increase the activity of beta-amyloid converting enzyme 1 (BACE1) protein causing Alzheimer's disease. The increased activity of BACE1 leads to neuronal damage and loss of memory and language skills, causing brain dysfunction.

Conventional diagnostic methods for Alzheimer's disease are based on the measurement of the level of amyloid beta, mainly $A\beta_{1-42}$ or $A\beta_{1-40}$. According to an ELISA technique for measuring the level of amyloid beta, a capture antibody capable of capturing the N-terminus (or C-terminus) of amyloid beta is located on a substrate and a detection antibody is allowed to bind to the C-terminus (or N-terminus) of the amyloid beta. The C-termini of amyloid beta oligomers recognized to be associated with Alzheimer's disease tend to aggregate. This tendency decreases the opportunity of the C-termini of the amyloid beta oligomers to react with the detection antibody when Alzheimer's disease is diagnosed by a conventional method. This phenomenon occurs because the number of the C-termini of the amyloid beta oligomers capable of reacting with the external antibody decreases as the size of the amyloid beta oligomers increases. Accordingly, although the total level of the amyloid beta is the same, the intensities of actually detected signals vary depending on the amount of the oligomers, which is disadvantageous in that the amyloid beta level cannot be accurately determined.

For the purpose of solving the above problems, it would be desirable to avoid the reaction of antibodies with the C-termini. However, existing ELISA techniques and some electrochemical sensors are based on the measurement of labeled detection antibodies, inevitably requiring the use of the C-termini. Some electrochemical sensors use the reaction of the N-terminus rather than the C-terminus of $A\beta_{1-x}$ but their detection results in plasma are inaccurate for the diagnosis of Alzheimer's disease.

PRIOR ART DOCUMENTS

Patent Documents

1. Korean Patent No. 100595494

SUMMARY OF THE INVENTION

The present invention intends to provide information relevant to the diagnosis of Alzheimer's disease and other neurodegenerative disorders.

An object of the present invention is to provide methods, biomarkers, kits, and devices for diagnosing, prognosing, predicting or treating Alzheimer's disease and other neurodegenerative disorders.

One embodiment of the present invention provides a method for providing information relevant to the diagnosis of a neurodegenerative disorder, including (i) obtaining a biological sample containing vesicles from a subject, (ii) measuring the level of amyloid beta in the biological sample using an antibody specific for the N-terminus of amyloid beta, and (iii) comparing the measured level of amyloid beta in the biological sample with the level of amyloid beta in a previously prepared control sample.

The method of the present invention may further include (iv) detecting an increased level of amyloid beta in the biological sample relative to the control sample to determine whether the subject has a neurodegenerative disorder.

The method of the present invention may further include isolating the vesicles from the biological sample.

The vesicles may be selected from the group consisting of exosomes, microparticles, microvesicles, nanosomes, extracellular vesicles, and ectosomes.

The exosomes may be selected from the group consisting of neuronal exosomes, astrocyte-derived exosomes, oligodendrocyte-derived exosomes, and microglia-derived exosomes.

The exosomes are preferably neuronal exosomes.

The N-terminus-specific antibody may bind to the N-terminus of amyloid beta.

The N-terminus-specific antibody may bind to all or a portion of the sequence of the first 16 amino acids from the N-terminus of amyloid beta.

The level of amyloid beta may be the protein, phosphorylated protein, mRNA or miRNA level of the amyloid beta.

The biological sample may be selected from the group consisting of blood, plasma, serum, saliva, urine, and mixtures thereof.

The neurodegenerative disorder may be selected from the group consisting of Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease.

The neurodegenerative disorder is preferably Alzheimer's disease (AD).

The antibody may be immobilized onto a biosensor.

The biosensor may be selected from the group consisting of electrochemical impedance spectrometry (EIS) sensor arrays, bead-based EIS sensors, enzyme linked immunoassay (ELISA) sensors, surface plasmon resonance (SPR)-based sensors, and field-effect transistor (FET) biosensors.

The level of amyloid beta in the biological sample may be determined by measuring an impedance or current change after the antibody specific for the N-terminus of the amyloid beta reacts with the amyloid beta present in the biological sample.

The method of the present invention may further include identifying the subject as having a neurodegenerative disorder when the impedance change is in the range of 40% to 80%.

The method of the present invention may further include identifying the subject as having a neurodegenerative disorder when the current change is in the range of 1 to 20%.

A further embodiment of the present invention provides a method for diagnosing or prognosing a neurodegenerative disorder in a subject, identifying a subject at risk of a neurodegenerative disorder, or prescribing a therapeutic regimen or predicting benefit from therapy in a subject having a neurodegenerative disorder, including (i) obtaining a biological sample containing vesicles from a subject, (ii) measuring the level of amyloid beta in the biological sample using an antibody specific for the N-terminus of amyloid beta, and (iii) comparing the measured level of amyloid beta in the biological sample with the level of amyloid beta in a previously prepared control sample.

Another embodiment of the present invention provides a set of biomarkers for diagnosing a neurodegenerative disorder in a subject, including an antibody specific for the N-terminus of amyloid beta to measure the level of amyloid beta in a biological sample containing vesicles from the subject.

Another embodiment of the present invention provides a kit for diagnosing a neurodegenerative disorder in a subject, including an antibody specific for the N-terminus of amyloid beta to measure the level of amyloid beta in a biological sample containing vesicles from the subject.

Still another embodiment of the present invention provides a device for diagnosing a neurodegenerative disorder, including (i) an injection port through which a biological sample containing vesicles from a subject is loaded, (ii) a reaction zone in which an antibody specific for the N-terminus of amyloid beta is present and reacts with the biological sample loaded through the injection port, and (iii) a measurement zone in which the level of amyloid beta in the biological sample is determined depending on the extent of reaction in the reaction zone.

The present invention can provide information relevant to the diagnosis of Alzheimer's disease and other neurodegenerative disorders.

The novel methods, biomarkers, kits, and devices of the present invention are effective in diagnosing, prognosing, predicting or treating Alzheimer's disease and other neurodegenerative disorders.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

Figure 1:
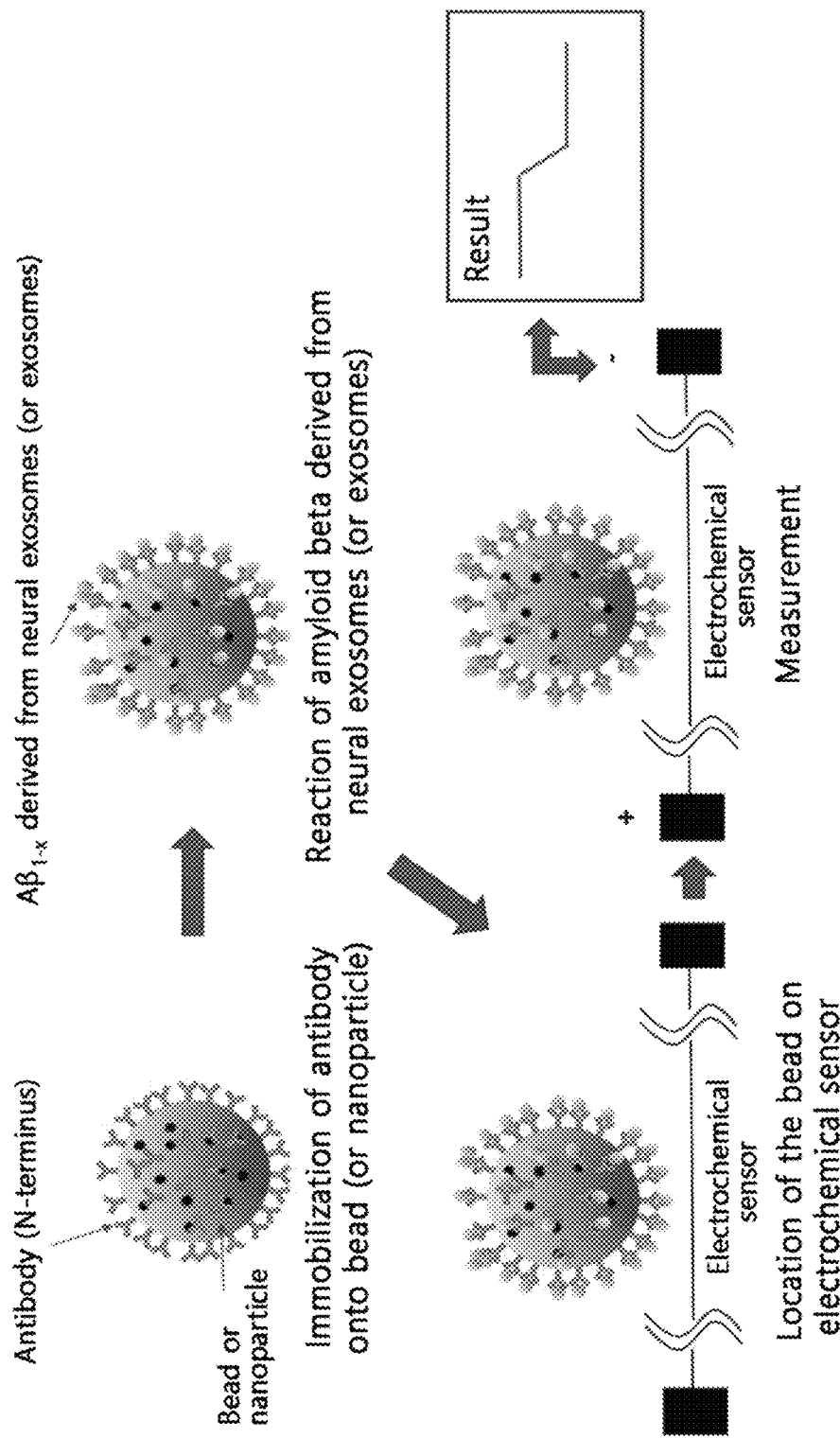
FIG. 1 is a conceptual diagram showing a method for measuring the amount of amyloid beta derived from neural exosomes using an electrochemical sensor after an antibody is immobilized onto the surface of a bead or nanoparticle.
Figure 2:
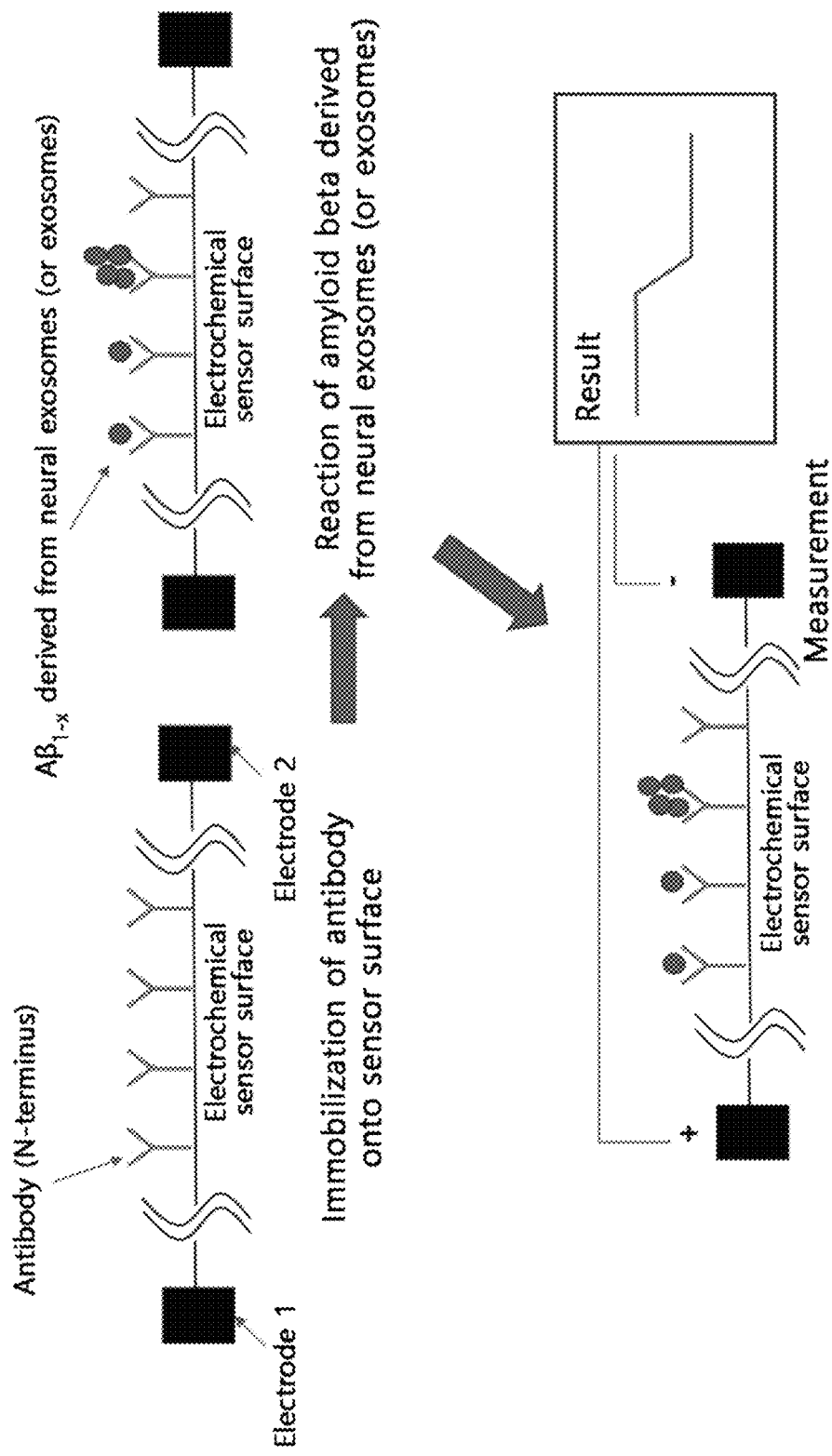
FIG. 2 is a conceptual diagram showing a method for measuring the amount of amyloid beta derived from neural exosomes using a resistance/current-based electrochemical sensor surface immobilized with an antibody.

It is to be understood that the invention is not limited to the particular methodologies, protocols, cell lines, assays, and reagents described herein, as these may vary. It is also to be understood that the terminology used herein is intended to describe particular embodiments of the present invention, and is in no way intended to limit the scope of the present invention as set forth in the appended claims.

It must be noted that as used herein and in the appended claims, the singular forms include plural references unless context clearly dictates otherwise. Thus, for example, a reference to "a fragment" includes a plurality of such fragments, a reference to an "antibody" is a reference to one or more antibodies and to equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art.

The present invention relates, in part, to the discovery that vesicle or exosomal biomarkers can be assayed to identify subjects having or likely to develop neurodegenerative disorders, including, for example, Alzheimer's disease (AD), multiple sclerosis (MS), and frontotemporal dementia (FTD).

The present invention is based, in part, on the discovery of unexpected increases in certain biomarkers in neuron-derived exosomes present in the circulation of subjects having neurodegenerative disease (e.g., Alzheimer's disease). The present invention demonstrates that exosomal levels of these biomarkers may be assayed to diagnose a neurodegenerative disorder in a subject having a neurodegenerative disease.

The present invention further shows that measurement of certain biomarkers in neuron-derived exosomes from a subject may be used to predict the subsequent development of a neurodegenerative disease (e.g., identify a subject at risk of developing a neurodegenerative disorder).

The present inventors have measured the amounts of amyloid beta in samples from patients with Alzheimer's disease, and as a result, found that the patients can be distinguished from healthy subjects by the type of the samples. That is, the patients can be more clearly distinguished from healthy subjects when the samples contain exosomes, especially neural exosomes, than when the samples contain plasma. The present invention has been accomplished based on this finding (see FIG. 6). In other words, the patients can be distinguished from healthy subjects by the amounts of amyloid beta in exosomes (or neural exosomes) as the samples rather than in the plasma samples.

Based on the present inventors' finding, patients can be distinguished from healthy subjects by measuring the amounts of amyloid beta in their exosome samples and comparing the measured amounts of amyloid beta with a previously prepared reference.

The exosomes may be isolated from a biological sample. The biological sample may be selected from, but not limited to, the group consisting of blood, plasma, serum, saliva, urine, and mixtures thereof. The exosomes are more preferably neural exosomes. Patients can be more clearly distinguished from healthy subjects by measuring the amounts of amyloid beta in their neural exosomes.

The present invention provides a set of biomarkers for assessing neurodegenerative status of a subject. In this embodiment, biomarker levels are assayed. The present invention is characterized in that the amount of amyloid beta in exosomes is measured. There is no particular restriction on the method for measuring the amount of amyloid beta. For example, the amount of amyloid beta can be determined by measuring an impedance or current change after the reaction of amyloid beta with an antibody (see FIGS. 6 and 7).

In one embodiment of the present invention, the neurodegenerative disorder may be Alzheimer's disease when the impedance change is in the range of 20% to 90%, 30% to 80%, 40% to 80%, 40% to 70%, 50% to 60% or 55% to 70%, preferably 60 to 65%. The neurodegenerative disorder may be Alzheimer's disease when the current change is in the range of 0.1% to 20%, 0.1% to 10%, 1% to 9%, 2% to 8%, 3% to 7%, or 4% to 6%, preferably 3 to 5%. These numerical ranges are drawn from experiments described in the Examples section that follows.

The present invention also provides compositions for use in the methods described herein. Such compositions may include small molecule compounds; peptides and proteins including antibodies or functionally active fragments thereof; and polynucleotides including small interfering ribonucleic acids (siRNAs), micro-RNAs (miRNAs), ribozymes, and anti-sense sequences. (See, e.g., Zeng (2003) Proc Natl Acad Sci USA 100:9779-9784; and Kurreck (2003) Eur J Biochem 270:1628-1644.)

The present invention further provides kits for diagnosing or prognosing a neurodegenerative disorder in a subject, identifying a subject at risk of a neurodegenerative disorder, or prescribing a therapeutic regimen or predicting benefit from therapy in a subject having a neurodegenerative disorder. In these embodiments, the kits comprise one or more antibodies which specifically binds exosomes, one or more antibodies which specifically bind a biomarker, one or more containers for collecting and or holding the biological sample, and an instruction for the kits use.

The section headings are used herein for organizational purposes only, and are not to be construed as in any way limiting the subject matter described herein.

Biological Sample

The present invention provides biomarkers and diagnostic and prognostic methods for Alzheimer's disease and other neurodegenerative disorders. Biomarker levels are determined in a biological sample obtained from a subject. In some embodiments, the biological sample of the invention can be obtained from blood. In some embodiments, about 1-10 mL of blood is drawn from a subject. In other embodiments, about 10-50 mL of blood is drawn from a subject. Blood can be drawn from any suitable area of the body, including an arm, a leg, or blood accessible through a central venous catheter.

In some embodiments, blood is collected following a treatment or activity. For example, blood can be collected following a medical exam. The timing of collection can also be coordinated to increase the number and/or composition of exosomes present in the sample. For example, blood can be collected following exercise or a treatment that induces vascular dilation.

Blood may be combined with various components following collection to preserve or prepare samples for subsequent techniques. For example, in some embodiments, blood is treated with an anticoagulant, a cell fixative, a protease inhibitor, a phosphatase inhibitor, a protein, a DNA, or an RNA preservative following collection. In some embodiments, blood is collected via venipuncture using vacuum collection tubes containing an anticoagulant such as EDTA or heparin. Blood can also be collected using a heparin-coated syringe and hypodermic needle. Blood can also be combined with components that will be useful for cell culture. For example, in some embodiments, blood is combined with cell culture media or supplemented cell culture media (e.g., cytokines).

Biological samples can also be obtained from other sources known in the art, including whole blood, serum, plasma, urine, interstitial fluid, peritoneal fluid, cervical swab, tears, saliva, buccal swab, skin, cerebrospinal fluid, or other tissues including, for example, brain tissues.

Enrichment or Isolation of Vesicles (Exosomes, Microparticles, Microvesicles, Nanosomes, Extracellular Vesicles, and Ectosomes)

Samples can be enriched for vesicles through positive selection, negative selection, or a combination of positive and negative selection. In some embodiments, vesicles are directly captured. In other embodiments, blood cells are captured and vesicles are collected from the remaining biological samples. In some embodiments, the vesicles enriched in the biological samples are exosomes, microparticles, microvesicles, nanosomes, extracellular vesicles, or ectosomes. In some embodiments, the vesicles enriched in the biological samples are neuron-derived exosomes, astrocyte-derived exosomes, oligodendrocyte-derived exosomes, and microglia-derived exosomes.

Samples can also be enriched for vesicles based on differences in the biochemical properties of vesicles. For example, samples can be enriched for vesicles based on antigen, nucleic acid, metabolic, gene expression, or epigenetic differences. In some of the embodiments based on antigen differences, antibody-conjugated magnetic or paramagnetic beads in magnetic field gradients or fluorescently labeled antibodies with flow cytometry are used. In some of the embodiments based on nucleic acid differences, flow cytometry is used.

In some of the embodiments based on metabolic differences, dye uptake/exclusion measured by flow cytometry or another sorting technology is used. In some of the embodiments based on gene expression, cell culture with cytokines is used. Samples can also be enriched for vesicles based on other biochemical properties known in the art. For example, samples can be enriched for vesicles based on pH or motility. Further, in some embodiments, more than one method is used to enrich for vesicles. In other embodiments, samples are enriched for vesicles using antibodies, ligands, or soluble receptors.

In other embodiments, surface markers are used to positively enrich vesicles in the sample. In some embodiments, the vesicles are exosomes, microparticles, microvesicles, nanosomes, extracellular vesicles, or ectosomes. In other embodiments, NCAM, CD171, CD9, CD63, CD81, diverse neuron or astrocyte adhesive proteins, microglial CD18/11, or CD3 T cell membrane cell surface markers are used to enrich for exosomes. In some embodiments, cell surface markers that are not found on vesicles populations are used to negatively enrich vesicles by depleting cell populations. Flow cytometry sorting may also be used to further enrich for exosomes using cell surface markers or intracellular or extracellular markers conjugated to fluorescent labels. Intracellular and extracellular markers may include nuclear stains or antibodies against intracellular or extracellular proteins preferentially expressed in vesicles. Cell surface markers may include antibodies against cell surface antigens that are preferentially expressed on exosomes (e.g., NCAM). In some embodiments, the cell surface marker is a neuron-derived exosome surface marker, including, for example, NCAM or CD171. In some embodiments, a monoclonal NCAM, CD9, CD63, CD81 or CD171 antibody is used to enrich or isolate exosomes from the sample. In certain aspects, the NCAM, CD9, CD63, CD81 or CD171 antibody is biotinylated. In this embodiment, biotinylated NCAM or CD171 antibody can form an antibody-exosome complex that can be subsequently isolated using streptavidin-agarose resin or beads. In other embodiments, the NCAM, CD9, CD63, CD81 or CD171 antibody is a monoclonal anti-human NCAM, CD9, CD63, CD81 or CD171 antibody.

In some embodiments, enriched vesicles from the biological sample are subsequently enriched for a specific type of vesicle. For example, the biological sample is enriched for exosomes and then the enriched exosomes are subsequently enriched for neural-derived exosomes. In some embodiments, the biological sample is enriched for individual neural cell sources of vesicles. In certain aspects, the neural cell sources of vesicles are microglia, neurons, or astrocytes.

In other embodiments, vesicles are isolated or enriched from a biological sample comprising: contacting a biological sample with an agent under conditions wherein a vesicle present in said biological sample binds to said agent to form a vesicle-agent complex; and isolating said vesicle from said vesicle-agent complex to obtain a sample containing said vesicle, wherein the purity of vesicles present in said sample is greater than the purity of vesicles present in said biological sample.

In certain embodiments, the agent is an antibody or a lectin. Lectins useful for forming a vesicle-lectin complex are described in U.S. Patent Application Publication No. 2012/0077263. In some embodiments, the vesicle is an exosome, a microparticle, a microvesicle, nanosomes, extracellular vesicles, or an ectosome. In some embodiments, the exosomes are neuron-derived exosomes, astrocyte-derived exosomes, oligodendrocyte-derived exosomes, or microglia-derived exosomes. In some embodiments, multiple isolating or enriching steps are performed. In certain aspects of the present embodiment, a first isolating step is performed to isolate exosomes from a blood sample and a second isolating step is performed to isolate neural-derived exosomes from other exosomes. In other embodiments, the vesicle portion of the vesicle-agent complex is lysed using a lysis reagent and the protein levels of the lysed vesicle are assayed. In some embodiments, the antibody-vesicle complex is created on a solid phase. In yet other embodiments, the methods further comprise releasing the vesicle from the antibody-vesicle complex. In certain embodiments, the solid phase is non-magnetic beads, magnetic beads, agarose, or sepharose. In other embodiments, the vesicle is released by exposing the antibody-vesicle complex to low pH between 3.5 and 1.5. In yet other embodiments, the released vesicle is neutralized by adding a high pH solution. In other embodiments, the released vesicle is lysed by incubating the released vesicles with a lysis solution.

In still other embodiments, the lysis solution contains inhibitors for proteases and phosphatases.

Neurodegenerative Disorders

The present invention provides methods for diagnosing or prognosing a neurodegenerative disorder in a subject, identifying a subject at risk of a neurodegenerative disorder, or prescribing a therapeutic regimen or predicting benefit from therapy in a subject having a neurodegenerative disorder.

In some embodiments, the neurodegenerative disorder is selected from the group consisting of: Alzheimer's disease (AD), vascular disease dementia, frontotemporal dementia (FTD), corticobasal degeneration (CBD), progressive supranuclear palsy (PSP), Lewy body dementia, tangle-predominant senile dementia, Pick's disease (PiD), argyrophilic grain disease, amyotrophic lateral sclerosis (ALS), other motor neuron diseases, Guam parkinsonism-dementia complex, FTDP-17, Lytico-Bodig disease, multiple sclerosis, traumatic brain injury (TBI), and Parkinson's disease.

In some embodiments, the present invention enables a medical practitioner to diagnose or prognose one or more neurodegenerative disorders in a subject. In other embodiments, the present invention enables a medical practitioner to rule out or eliminate one or more neurodegenerative diseases as a diagnostic possibility. In yet other embodiments, the present invention enables a medical practitioner to identify a subject at risk of developing a neurodegenerative disorder. In other embodiments, the present invention enables a medical practitioner to predict whether a subject will later develop a neurodegenerative disorder. In further embodiments, the present invention enables a medical practitioner to prescribe a therapeutic regimen or predict benefit from therapy in a subject having a neurodegenerative disorder.

Biomarkers

Biomarker levels are assayed in a biological sample obtained from a subject having or at-risk of having a neurodegenerative disorder (e.g., Alzheimer's disease). In some embodiments, the biomarker is amyloid beta. Particularly, the biomarker may be the N-terminus of amyloid beta. In the present specification (including the drawings), "Abeta 1-x" means Abeta that is attached to an antibody specific for the N-terminus of amyloid beta. The portion consisting of the upstream 16 amino acids of amyloid beta (Abeta) may act as the N-terminus. For example, in the case where Abeta is cleaved to expose its third amino acid, the third amino acid may act as the N-terminus. Alternatively, Abeta may be cleaved to separate the portion consisting of the downstream sixth to 39th amino acids. In this case, the sixth amino acid may act as the N-terminus and the 39th amino acid may act as the C-terminus.

In other embodiments, the biomarker is selected from the group consisting of phosphorylated Tau, A⊕1-42, TDP-43, α-synuclein, SOD-1, FUS, FKBP51, IRS-1, phosphorylated IRS-1, CTSD, LAMP1, UBP, HSP70, NSE, NFL, CD9, CD63, CD81, and CD171.

In some embodiments, biomarker levels of the present invention are measured by determining the gene expression of the biomarker. In certain embodiments, gene expression changes are measured by determining the expression level of amyloid beta. In certain aspects, gene expression of the biomarker is determined using PCR, microarray, or sequencing. In some embodiments, the expression level of the biomarker is determined by measuring the mRNA or miRNA level of the biomarker.

One of ordinary skill in the art has several methods and devices available for the detection and analysis of the markers of the instant invention. With regard to polypeptides or proteins in patient test samples, immunoassay devices and methods are often used. These devices and methods can utilize labeled molecules in various sandwich, competitive, or non-competitive assay formats, to generate a signal that is related to the presence or amount of an analyte of interest. Additionally, certain methods and devices, such as biosensors and optical immunoassays, may be employed to determine the presence or amount of analytes without the need for a labeled molecule.

Preferably, the markers are analyzed using an immunoassay, although other methods are well known to those skilled in the art (for example, the measurement of marker RNA levels). The presence or amount of a marker is generally determined using antibodies specific for each marker and detecting specific binding. Any suitable immunoassay may be utilized, for example, enzyme-linked immunoassays (ELISA), radioimmunoassay (RIAs), competitive binding assays, planar waveguide technology, and the like. Specific immunological binding of the antibody to the marker can be detected directly or indirectly. Direct labels include fluorescent or luminescent tags, metals, dyes, radionuclides, and the like, attached to the antibody. Indirect labels include various enzymes well known in the art, such as alkaline phosphatase, horseradish peroxidase and the like.

The use of immobilized antibodies specific for the markers is also contemplated by the present invention. The antibodies could be immobilized onto a variety of solid supports, such as magnetic or chromatographic matrix particles, the surface of an assay place (such as microtiter wells), pieces of a solid substrate material (such as plastic, nylon, paper), and the like. An assay strip could be prepared by coating the antibody or a plurality of antibodies in an array on solid support. This strip could then be dipped into the test sample and then processed quickly through washes and detection steps to generate a measurable signal, such as a colored spot.

The analysis of a plurality of markers may be carried out separately or simultaneously with one test sample. Several markers may be combined into one test for efficient processing of a multiple of samples. In addition, one skilled in the art would recognize the value of testing multiple samples (for example, at successive time points) from the same individual. Such testing of serial samples will allow the identification of changes in marker levels over time. Increases or decreases in marker levels, as well as the absence of change in marker levels, would provide useful information about the disease status that includes, but is not limited to identifying the approximate time from onset of the event, the presence and amount of salvageable tissue, the appropriateness of drug therapies, the effectiveness of various therapies, identification of the severity of the event, identification of the disease severity, and identification of the patient's outcome, including risk of future events.

An assay consisting of a combination of the markers referenced in the instant invention may be constructed to provide relevant information related to differential diagnosis. Such a panel may be constructed using 1, 2, 3, 4, 5, 6, 7, 8, 9, 10, 15, 20, or more or individual markers. The analysis of a single marker or subsets of markers comprising a larger panel of markers could be carried out methods described within the instant invention to optimize clinical sensitivity or specificity in various clinical settings. The ratio of P-5312-IRS-1 and P-panY-IRS-1 (R or insulin resistance index) may be used to predict risk or diagnosis of a neurodegenerative disorder.

The analysis of markers could be carried out in a variety of physical formats as well. For example, the use of microtiter plates or automation could be used to facilitate the processing of large numbers of test samples. Alternatively, single sample formats could be developed to facilitate immediate treatment and diagnosis in a timely fashion, for example, in ambulatory transport or emergency room settings. Particularly useful physical formats comprise surfaces having a plurality of discrete, addressable locations for the detection of a plurality of different analytes. Such formats include protein microarrays, or "protein chips" and capillary devices.

Biomarkers of the present invention serve an important role in the early detection and monitoring of neurodegenerative disorders (e.g., Alzheimer's disease). Markers of such disorders are typically substances found in a bodily sample that can be measured. The measured amount can correlate to underlying disorder or disease pathophysiology, presence or absence of a neurodegenerative disorder, probability of a neurodegenerative disorder in the future. In patients receiving treatment for their condition, the measured amount will also correlate with responsiveness to therapy.

In some embodiments, the biomarker is measured by a method selected from the group consisting of immunohistochemistry, immunocytochemistry, immunofluorescence, immunoprecipitation, western blotting, and ELISA.

Clinical Assay Performance

The methods of the present invention may be used in clinical assays to diagnose or prognose a neurodegenerative disorder in a subject, identify a subject at risk of a neurodegenerative disorder, and/or for prescribing a therapeutic regimen or predicting benefit from therapy in a subject having a neurodegenerative disorder. Clinical assay performance can be assessed by determining the assay's sensitivity, specificity, area under the ROC curve (AUC), accuracy, positive predictive value (PPV), and negative predictive value (NPV). Disclosed herein are assays for diagnosing or prognosing a neurodegenerative disorder in a subject, identifying a subject at risk of a neurodegenerative disorder, or for prescribing a therapeutic regimen or predicting benefit from therapy in a subject having a neurodegenerative disorder.

The clinical performance of the assay may be based on sensitivity. The sensitivity of an assay of the present invention may be at least about 40%, 45%, 50%, 55%, 60%, 65%, 70%, 75%, 80%, 85%, 90%, 95%, 99%, or 100%. The clinical performance of the assay may be based on specificity. The specificity of an assay of the present invention may be at least about 40%, 45%, 50%, 55%, 60%, 65%, 70%, 75%, 80%, 85%, 90%, 95%, 99%, or 100%. The clinical performance of the assay may be based on area under the ROC curve (AUC). The AUC of an assay of the present invention may be at least about 0.5, 0.55, 0.6, 0.65, 0.7, 0.75, 0.8, 0.85, 0.9, or 0.95. The clinical performance of the assay may be based on accuracy. The accuracy of an assay of the present invention may be at least about 40%, 45%, 50%, 55%, 60%, 65%, 70%, 75%, 80%, 85%, 90%, 95%, 99%, or 100%.

Compositions

Compositions useful in the methods of the present invention include compositions that specifically recognize a biomarker associated with a neurodegenerative disorder, wherein the biomarker is amyloid beta.

In some embodiments, the composition enhances the activity of one or more amyloid beta peptides. In other embodiments, the composition reduces the activity of one or more amyloid beta peptides. In yet other embodiments, the composition is selected from the group consisting of a peptide, a nucleic acid, an antibody, and a small molecule.

In certain embodiments, the present invention relates to compositions that specifically detect a biomarker associated with a neurodegenerative disorder.

In some embodiments, the composition comprises an antibody, where the antibody specifically binds to a biomarker or vesicles of the invention. The present invention is characterized by the use of amyloid beta, particularly the N-terminus of amyloid beta, as a biomarker. To this end, it is preferred that the antibody is specific for the N-terminus of amyloid beta. That is, the antibody is capable of binding to the N-terminus of amyloid beta.

The term "antibody" as used herein and further discussed below is intended to include fragments thereof which are also specifically reactive with a biomarker or vesicle (e.g., exosome). Antibodies can be fragmented using conventional techniques and the fragments can be screened for utility in the same manner as described above for whole antibodies. For example, F(ab)2 fragments can be generated by treating antibody with pepsin. The resulting F(ab)2 fragment can be treated to reduce disulfide bridges to produce Fab fragments. Antigen-binding portions may also be produced by recombinant DNA techniques or by enzymatic or chemical cleavage of intact antibodies. Antigen-binding portions include, inter alia, Fab, Fab', F(ab')2, Fv, dAb, and complementarity determining region (CDR) fragments, single-chain antibodies (scFv), single domain antibodies, bispecific antibodies, chimeric antibodies, humanized antibodies, diabodies and polypeptides that contain at least a portion of an immunoglobulin that is sufficient to confer specific antigen binding to the polypeptide. In certain embodiments, the antibody further comprises a label attached thereto and able to be detected (e.g., the label can be a radioisotope, fluorescent compound, enzyme or enzyme co-factor).

In certain embodiments, an antibody of the invention is a monoclonal antibody, and in certain embodiments, the invention makes available methods for generating novel antibodies that specifically bind the biomarker or the exosome of the invention. For example, a method for generating a monoclonal antibody that specifically binds a biomarker or exosome, may comprise administering to a mouse an amount of an immunogenic composition comprising the biomarker or exosome, or fragment thereof, effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the biomarker or exosome. Once obtained, a hybridoma can be propagated in a cell culture, optionally in culture conditions where the hybridoma-derived cells produce the monoclonal antibody that binds specifically to the biomarker or exosome. The monoclonal antibody may be purified from the cell culture.

The term "specifically reactive with" as used in reference to an antibody is intended to mean, as is generally understood in the art, that the antibody is sufficiently selective between the antigen of interest (e.g., a biomarker or exosome) and other antigens that are not of interest. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ or less.

Antibodies can be generated to bind specifically to an epitope of an exosome or a biomarker of the present invention, including, for example, neuron-derived exosome and amyloid beta.

In addition, the techniques used to screen antibodies in order to identify a desirable antibody may influence the properties of the antibody obtained. A variety of different techniques are available for testing interaction between antibodies and antigens to identify particularly desirable antibodies. Such techniques include ELISAs, surface plasmon resonance binding assays (e.g., the Biacore binding assay, Biacore AB, Uppsala, Sweden), sandwich assays (e.g., the paramagnetic bead system of IGEN International, Inc., Gaithersburg, Md.), western blots, immunoprecipitation assays, immunocytochemistry, and immunohistochemistry.

In some embodiments, the present invention relates to compositions used for treating or preventing a neurodegenerative disorder.

As detailed elsewhere herein, the present invention is based upon the findings that amyloid beta is implicated in the pathology of a variety of neurodegenerative disorders, such as, for example, Alzheimer's disease.

Methods of Treatment

The present invention provides methods of treating a neurodegenerative disorder in a subject, comprising administering to the subject an effective amount of a composition, wherein the composition reduces the level of amyloid beta. In other embodiments, the composition enhances the activity of one or more amyloid beta peptides. In yet other embodiments, the composition reduces the activity of one or more amyloid beta peptides. In other embodiments, the composition is selected from the group consisting of a peptide, a nucleic acid, an antibody, and a small molecule.

Kits

Another aspect of the invention encompasses kits for detecting or monitoring a neurodegenerative disorder in a subject. A variety of kits having different components are contemplated by the current invention. Generally speaking, the kit will include the means for quantifying one or more biomarkers in a subject. In another embodiment, the kit will include means for collecting a biological sample, means for quantifying one or more biomarkers in the biological sample, and instructions for use of the kit contents. In certain embodiments, the kit comprises a means for enriching or isolating exosomes in a biological sample. In further aspects, the means for enriching or isolating exosomes comprises reagents necessary to enrich or isolate exosomes from a biological sample. In certain aspects, the kit comprises a means for quantifying the amount of a biomarker. In further aspects, the means for quantifying the amount of a biomarker comprises reagents necessary to detect the amount of a biomarker.

The present invention will be explained in more detail with reference to the following examples. These examples are provided solely to illustrate the claimed invention. The present invention is not limited in scope by the exemplified embodiments.

EXAMPLE 1. PREPARATION OF EXOSOME SAMPLES 1.1. Isolation of Exosomes from Blood Exosomes were isolated from blood by the following procedure. First, blood cell-free plasma was reacted with a calcium reprecipitating agent in a ratio of 1:3 and the reaction mixture was mixed with a thrombin solution. The resulting solution was centrifuged to precipitate cellulose. The cellulose-free supernatant was diluted with PBS. The dilute solution was reacted with a solution of ExoQuick™ for 1 h. Thereafter, the supernatant was removed by centrifugation to obtain pellets of exosomes. The isolated exosomes were stored in PBS solution before use.

1.2. Isolation of Neural Exosomes

The exosomes isolated in 1.1 were derived from diverse cells. For this reason, the exosomes were secondarily purified to isolate only neural exosomes. The exosome solution prepared in 1.1 was diluted with a mixture of a PBS solution and 3% bovine serum albumin (BSA), and a solution of a biotinylated antibody reactive with a neuronal membrane-specific protein was reacted with the dilute exosome solution. The reactive antibody was used to selectively capture neural exosomes. Thereafter, to the reaction solution were added 40 µl of a 3% BSA solution and 20 µl of a solution of a streptavidin-agarose resin. The reaction was carried out at 40° C. for 10 min. The supernatant was removed by centrifugation. The pH was lowered by the addition of a glycine-HCl buffer solution (50 mM, pH 3.0), the solution was sufficiently mixed using a vortexer, followed by centrifugation to isolate exosomes from the biotin-streptavidin-agarose resin. The supernatant containing exosomes was transferred to a new container and neutralized with a Tris-HCl buffer solution (1 M, pH 8.6). The purified neural exosome solution was stored in PBS solution before use in subsequent experiments.

1.3. Extraction of $A\beta_{1-x}$ from Neural Exosomes

Amyloid beta was extracted just before measurement because of its tendency to degrade. First, the neural exosome solution stored at 80° C. was dissolved at 4° C. for about 10 min. RIPA buffer was added to the neural exosome solution in a ratio of 1:1 and the neural exosomes were disrupted by sonication for 1 min while maintaining a temperature of 4° C. During this procedure, the exosomal membranes were lysed to obtain a mixture solution of extracted $A\beta_{1-x}$.

Figure 3:
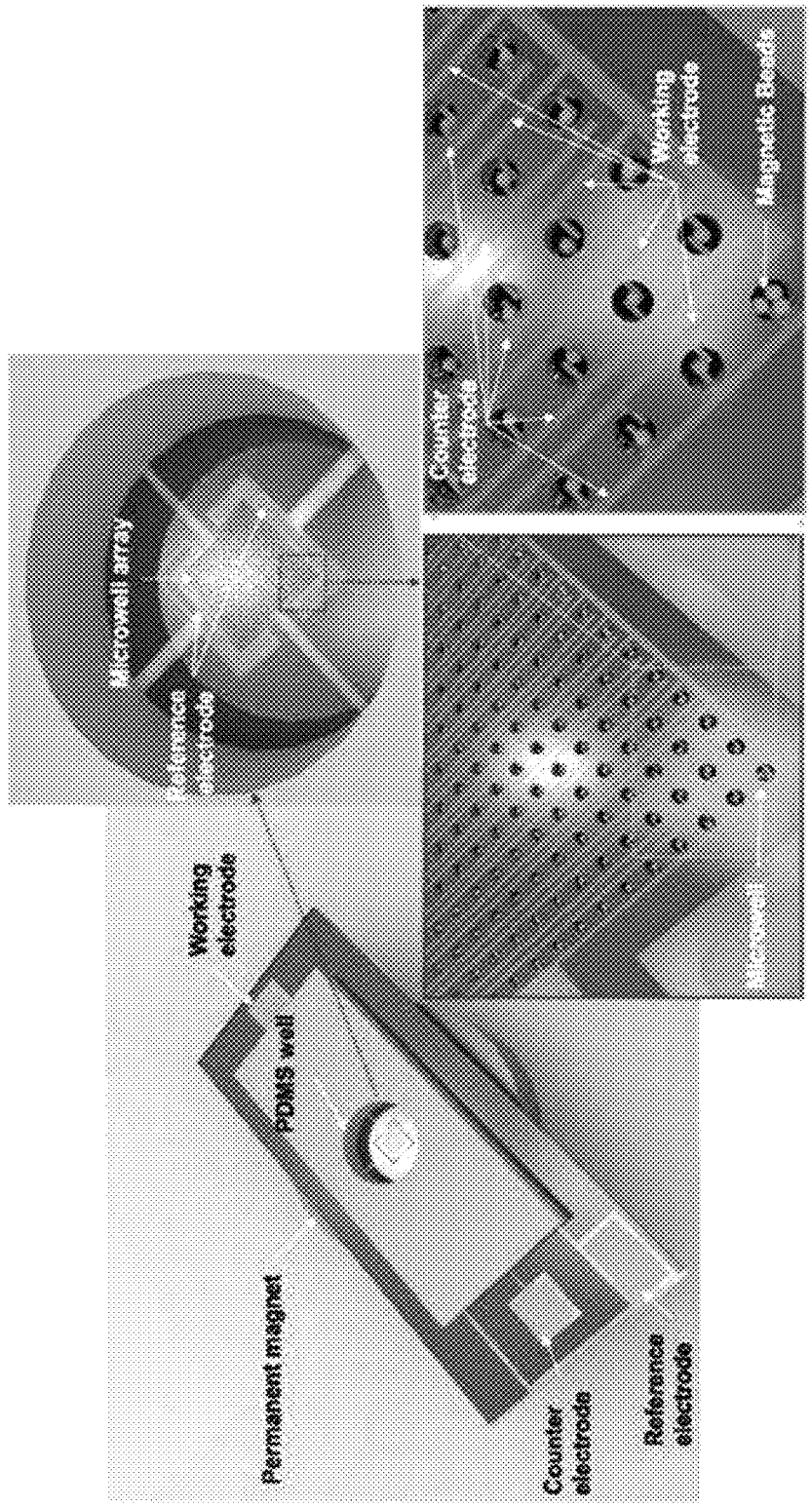
FIG. 3 is a conceptual diagram showing the location of one or more captured beads in each patterned microwell.
Figure 4:
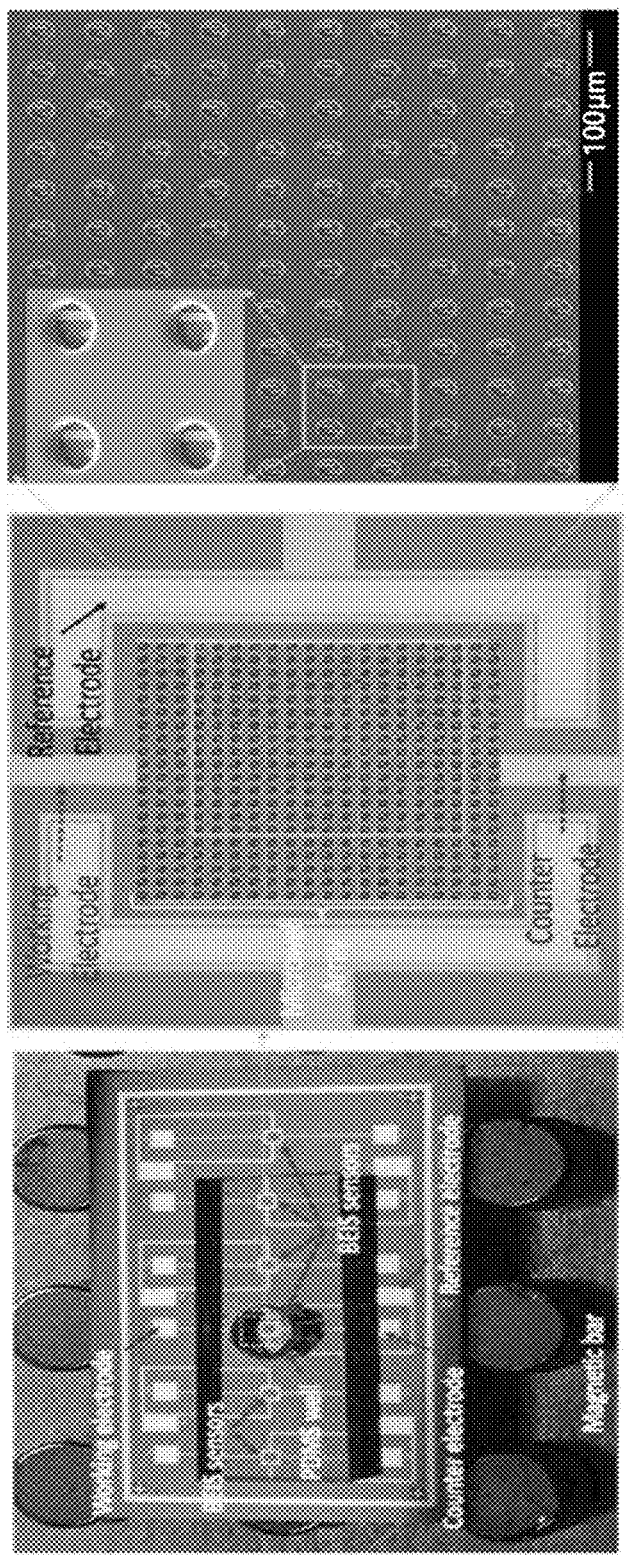
FIG. 4 shows an actual image of a device including patterned microwells attached with an antibody.
Figure 5:
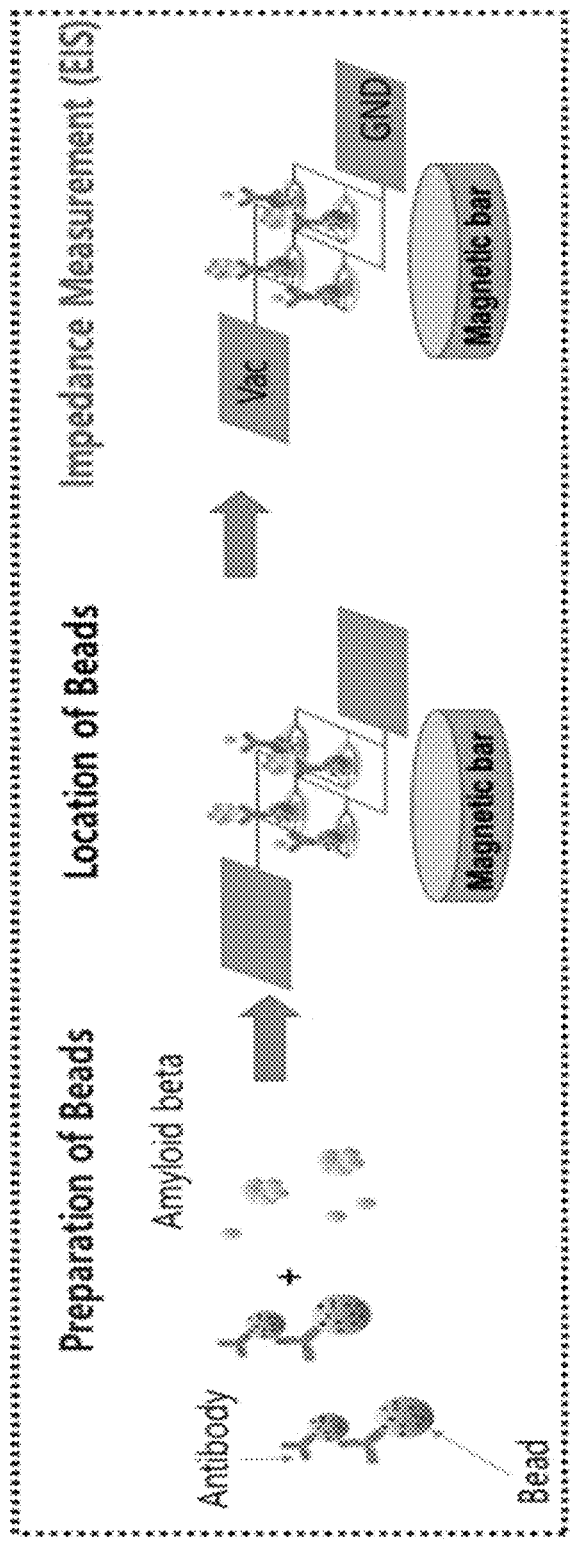
FIG. 5 shows the concept of impedance measurement after amyloid beta is allowed to react with an antibody present on beads.

EXAMPLE 2. DETECTION $A\beta_{1-x}$ EXTRACTED FROM NEURAL EXOSOMES USING DEVICE INCLUDING BEADS OR NANOPARTICLES SURFACE TREATED WITH ANTIBODY 2.1. Fabrication of Sensor Using Beads A sensor using beads was fabricated. First, i) electrode shapes were patterned on a silicon substrate having a silicon dioxide layer as an oxide film by a photolithographic process, ii) titanium-platinum electrodes were stacked by electron beam evaporation and the remaining portion was removed by a lift-off process, iii) microwells were patterned using a Su8 photoresist to confine beads in the subsequent process, to complete a bottom plate structure of the sensor, iv) PDMS was formed to a thickness of ~2 mm and a 2-3 mm hole was formed with a puncher to form a PDMS well into which a sample was loaded from the outside, and v) oxygen plasma treatment was performed to bond the bottom plate structure to the PDMS well, completing device fabrication. FIG. 3 is a conceptual diagram showing the location of one or more captured beads in each patterned microwell and FIG. 4 shows an actual image of the device.

2.2. Methods

A solution (200 µl) of microbeads (M-280 Tosylactivated magnetic beads, Dynabeads) surface activated with functional groups capable of reacting with an antibody was centrifuged at room temperature to precipitate the beads. The beads were fixed using a magnetic bar and the supernatant was removed. A 0.1 mM phosphate buffered saline solution was filtered through a porous membrane filter (pore size 0.2 µm). After filtration, 1 ml of the buffer solution was added to the remaining beads. This washing procedure was done to remove residues other than the beads. After washing three times, the supernatant was removed. The beads were sufficiently mixed with 720 µl of a 0.1 mM phosphate buffered saline solution and 80 µl of an antibody solution. The resulting bead solution was allowed to react at 37° C. for 24 h. Thereafter, the bead solution was washed with PBS buffer and Tris buffer, which were previously prepared by filtration using the same filter. The supernatant was removed from the bead solution, the supernatant-free bead solution was sufficiently mixed with the PBS buffer at room temperature for 5 min, the mixture was washed with the Tris buffer, and the reaction was allowed to proceed at 37° C. for 4 h. The supernatant was again removed from the washed bead solution. The remaining beads were stored in 200 µl of a filtered PBS solution at 4° C.

The bead solution was diluted with PBS buffer in a ratio of 1:150. The bead solution was reacted with the solution of extracted $A\beta_{1-x}$ obtained in Example 1 in a ratio of 1:2 for 40 min. Then, the beads were fixed using a magnetic bar and the supernatant was removed. Thereafter, the supernatant-free solution was washed once with PBS buffer, sufficiently mixed, and washed additional three times with a PBS solution.

The beads were placed in the pre-patterned microwells using a magnetic bar located under the patterned microwells of the device. Thereafter, an impedance change in the device was measured with impedance spectroscopy using Autolab PGSTAT302N electrochemistry workstation.

2.3. Results

Figure 6:
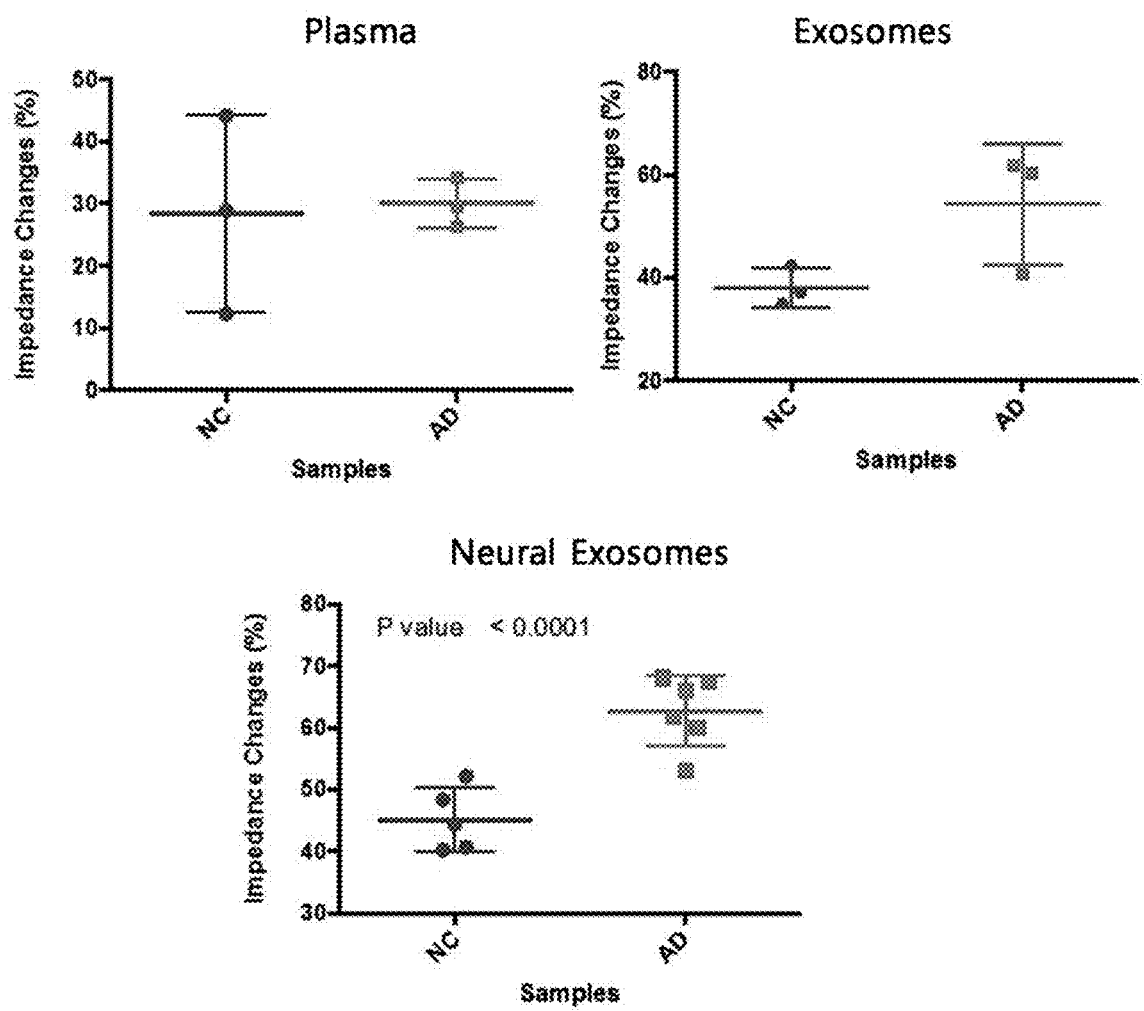
FIG. 6 shows impedance changes in a device including beads surface treated with an antibody to distinguish amyloid beta peptides derived from plasma, exosomes, and neural exosomes.
Figure 7:
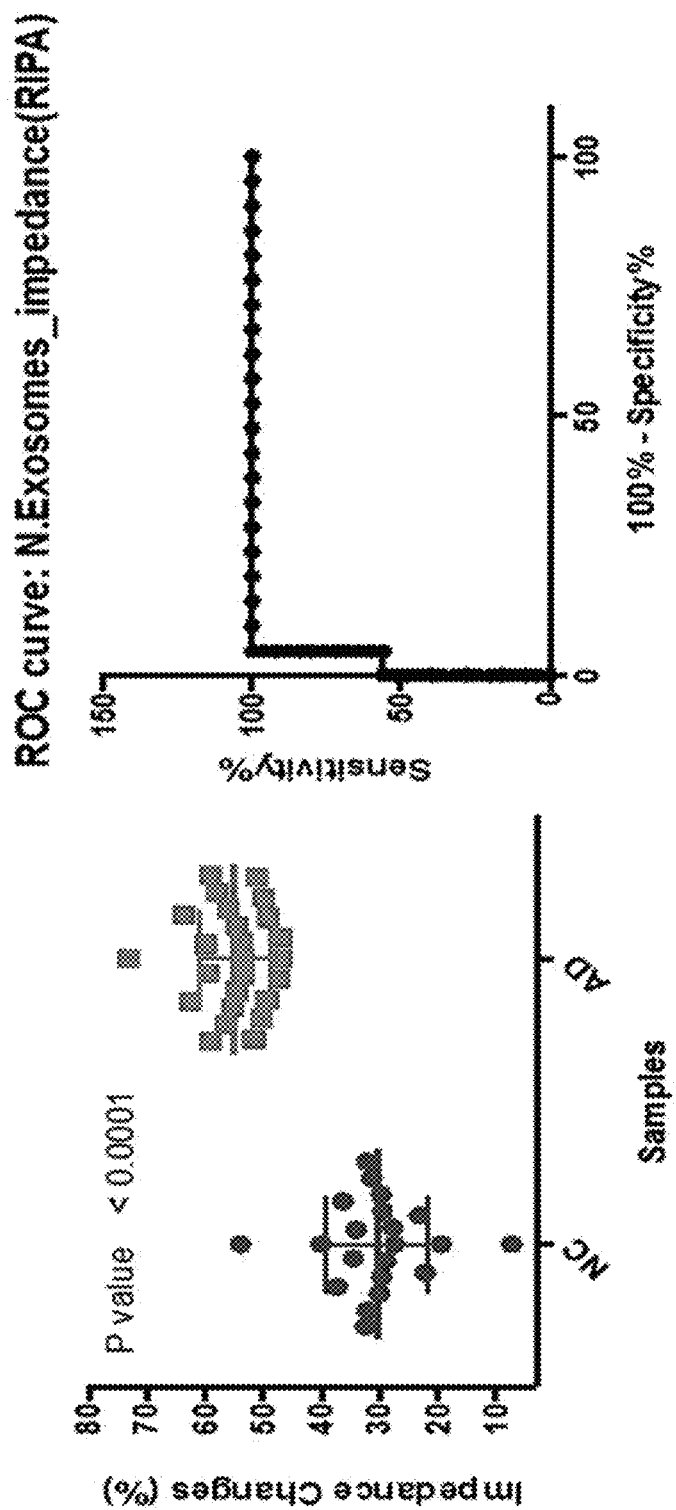
FIG. 7 shows impedance changes in 47 samples (left panel) and sensitivities and specificities measured using ROC charts (right panel)
Figure 8:
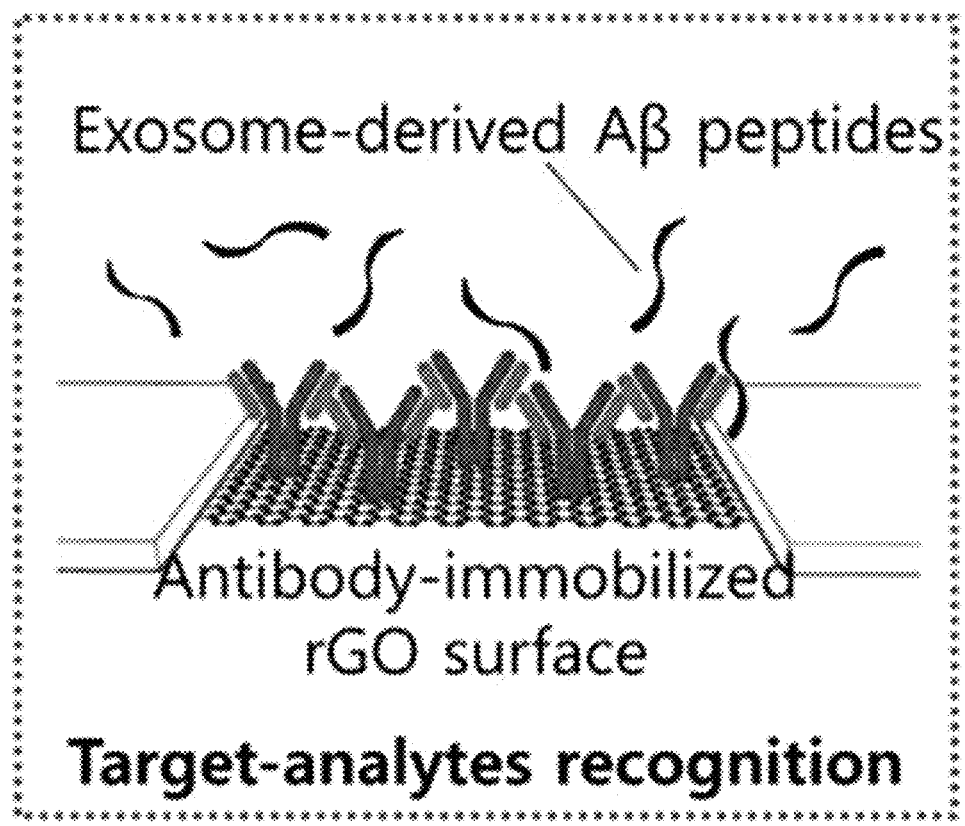
FIG. 8 is a conceptual diagram showing the binding of exosome-derived amyloid beta peptides to the surface of antibody-immobilized reduced graphene oxide (GO)
Figure 9:
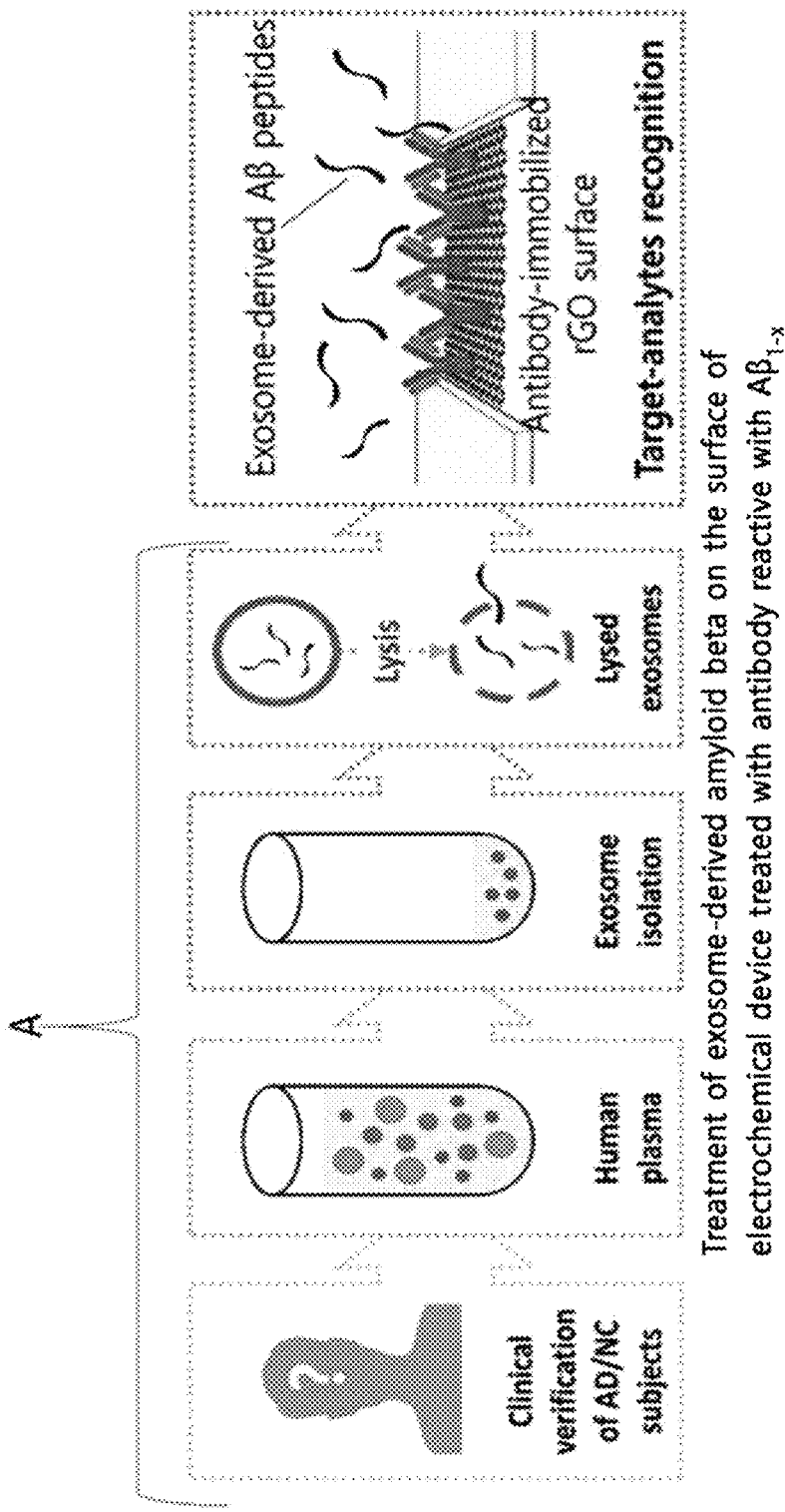
FIG. 9 is a conceptual diagram showing a method for measuring the amount of amyloid beta by collecting a sample from a subject, isolating exosomes from the human plasma, lysing the exosomes to extract amyloid beta, and reacting the amyloid beta with antibody-immobilized reduced GO.
Figure 10:
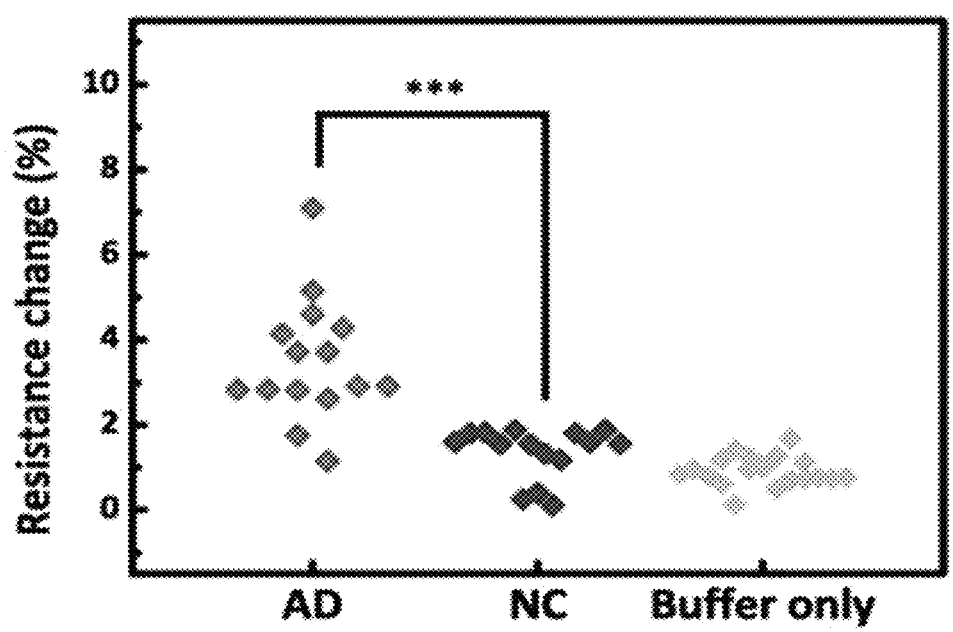
FIG. 10 shows resistance values measured using a reduced GO sensor.

The utility of exosomes and neural exosomes was confirmed. To this end, Aβ was extracted from plasma, exosomes, and neural exosomes and an experiment was conducted to investigate whether the Aβ derived from exosomes was distinguishable from the Aβ derived from neural exosomes. There was no difference in impedance change between the Aβ extracted from plasma and a control. For the Aβ derived from exosomes, increased impedance changes were observed in patients with Alzheimer's disease. The Aβ derived from neural exosomes showed pronounced differences in impedance change in patients with Alzheimer's disease without overlapping ranges compared to the Aβ derived from exosomes (FIG. 6).

The above procedure was repeated using an increased number (47) of exosome samples to further clarify the above results. As a result, the impedance changes in patients with Alzheimer's disease (AD) were clearly distinguished from those in the negative control (NC) (see the left panel of FIG. 7), indicating very high accuracy of the method based on the use of Aβ derived from exosomes compared to existing blood-based methods. Sensitivities and specificities measured using ROC charts were found to be 100% and 90%, respectively (see the right panel of FIG. 7).

These results concluded that the measurement of impedance changes as a result of the reaction of amyloid beta extracted from neural exosomes with antibody-attached beads or nanoparticles enables the diagnosis of patients with Alzheimer's disease with high accuracy.

EXAMPLE 3. USE OF RESISTANCE/CURRENT-BASED ELECTROCHEMICAL SENSORS—FET AND RESISTANCE SENSORS

3.1. Preparation of Sensor Using Reduced Graphene Oxide (rGO)—rGO Thin Film Coating and Sensor Fabrication Graphene oxide (GO) was prepared by the Modified Hummers method and was exfoliated into flakes by ultrasonic disintegration. Relatively large flakes were settled down by centrifugation and only relatively thin flakes were stored in ultrapure Milli-Q water before use. A GO thin film was coated on a silicon substrate having a silicon dioxide layer as an oxide film by meniscus-dragging deposition (MDD). First, residue was removed from the surface of a glass plate by the piranha treatment. The GO solution was dropped onto the silicon substrate, and the glass plate was brought into contact with the substrate and the solution and allowed to move at a constant rate of 20 mm/s while maintaining an angle of 30°. This procedure was repeated at least 20 times to form a GO thin film. Hydriodic acid gas was added to the GO thin film at 80° C. for 3 h to reduce the GO. Thereafter, a photoresist mask was formed on the rGO thin film by a photolithographic process and the remaining portion was removed by a reactive ion etching process using an oxygen plasma (300 W, 30 sec). After etching, the mask was removed by a lift-off process. Patterns for connecting chromium-gold electrodes were formed at both ends of the remaining rGO thin film by a photolithographic process. The electrodes were stacked by electron beam evaporation and the remaining portion was removed by a lift-off process, completing the fabrication of an rGO device. The rGO device was treated with an oxygen plasma to reactivate functional groups where an antibody is to be attached to the rGO thin film in the subsequent process.

3.2. Preparation of Sensor Using Reduced Graphene Oxide (rGO)—Surface Treatment The rGO thin film of the device was exposed to 20 μl of a solution of 1-ethyl-3-[3-dimethylaminopropyl]-carbodiimide (EDC, 2 mM, Sigma Aldrich, USA), a solution of N-succinimide (NHS, 8 mM, Sigma Aldrich, USA), and a 10 mM PBS solution for 1 h. Thereafter, a mixture solution of an antibody capable of capturing $Aβ_{1-x}$ (6E10 antibody, Abcam), EDC, and NHS was allowed to react with the rGO surface for 2 h to attach the antibody to the rGO surface.

3.3. Methods

The $Aβ_{1-x}$ sample extracted from neural exosomes in Example 1 was allowed to react with the surface of the rGO sensor fabricated in 3.1 and 3.2 for 30 min. Thereafter, resistance values were measured using a semiconductor parameter analyzer.

3.4. Results

Neural exosomes were isolated from 30 samples. Aβ was extracted from the neural exosomes and used for the subsequent experiment. As a result, high resistance changes (%) were observed in patients with Alzheimer's disease (AD) compared to in the control group.

In conclusion, the measurement of resistance changes as a result of the reaction of amyloid beta extracted from neural exosomes with the antibody-immobilized rGO sensor enables the diagnosis of Alzheimer's disease.

What is claimed is:

1. A method of diagnosing a subject with Alzheimer's disease (AD), comprising:
   obtaining a biological sample containing exosomes from the subject;
   isolating the exosomes from the biological sample;
   determining a level of amyloid beta in the exosomes by using an antibody specific for the N-terminus of amyloid beta, the determining step comprising:
      providing a bead or nanoparticle having a N-terminus-specific antibody immobilized on a surface thereof;
      contacting the isolated exosomes with said bead or nanoparticle; and
      measuring an amount of amyloid beta bound to said bead or nanoparticle using an electrochemical impedance spectrometry (EIS) sensor, by measuring an impedance change or current change after the N-terminus-specific antibody reacts with the amyloid beta present in the isolated exosomes;
   obtaining a reference level of amyloid beta present in isolated exosomes from a normal control not having Alzheimer's disease;
   comparing the level of amyloid beta measured in the isolated exosomes from the biological sample with the reference level of amyloid beta present in the isolated exosomes from the normal control; and
   diagnosing the subject as having the Alzheimer's disease (AD) if the level of amyloid beta in the biological sample is higher than the reference level of amyloid beta.

2. The method according to claim 1, wherein the exosomes are selected from the group consisting of neuronal exosomes, astrocyte-derived exosomes, oligodendrocyte-derived exosomes, and microglia-derived exosomes.

3. The method according to claim 1, wherein the exosomes are neuronal exosomes.

4. The method according to claim 1, wherein the N-terminus-specific antibody binds to all or a portion of the sequence of the first 16 amino acids from the N-terminus of amyloid beta.

5. The method according to claim 1, wherein the biological sample is selected from the group consisting of blood, plasma, serum, saliva, urine, and mixtures thereof.

6. The method according to claim 1, wherein the subject is identified as having the Alzheimer's disease (AD) when the impedance change is in the range of 40% to 80%.

7. The method according to claim 1, wherein the biological sample is plasma.

8. The method according to claim 1, further comprising lysing the isolated exosomes and contacting the lysed exosomes with said bead or nanoparticle.

* * * * *